(12) United States Patent
Suzuki et al.

(10) Patent No.: US 6,723,696 B1
(45) Date of Patent: Apr. 20, 2004

(54) BONE RESORPTION INHIBITORS

(75) Inventors: Kazuo Suzuki, Misaki-machi (JP); Satoshi Yamagoe, Kashiwa (JP); Tooru Yamakawa, Tokyo (JP)

(73) Assignee: Japan as represented by Secretary of National Institute of Infectious Diseases, Tokyo (JP)

( * ) Notice: Subject to any disclaimer, the term of this patent is extended or adjusted under 35 U.S.C. 154(b) by 0 days.

(21) Appl. No.: 09/868,953

(22) PCT Filed: Dec. 20, 1999

(86) PCT No.: PCT/JP99/07152

§ 371 (c)(1),
(2), (4) Date: Sep. 19, 2001

(87) PCT Pub. No.: WO00/37093

PCT Pub. Date: Jun. 29, 2000

(30) Foreign Application Priority Data

Dec. 22, 1998 (JP) .............................. 10-363727

(51) Int. Cl.[7] ........................ A61K 38/16; C07K 14/00; C07K 14/935
(52) U.S. Cl. ............................ 514/2; 514/12; 530/350; 530/300; 435/4
(58) Field of Search ................................ 530/350, 300; 514/2, 12; 435/4

(56) References Cited

U.S. PATENT DOCUMENTS 5,929,224 A    7/1999  Suzuki et al. .............. 536/235
6,306,608 B1 * 10/2001  Arai

FOREIGN PATENT DOCUMENTS

| EP | 0 723 016 A2 | 7/1996 |
| JP | 08-027020 | 1/1996 |
| JP | 08-140683 | 4/1998 |
| JP | 10-146189 | 6/1998 |
| KR | 97065715 A | * 10/1997 |

OTHER PUBLICATIONS

Wells, 1990, Biochemistry 29:8509–8517.*
Ngo et al., 1994, The Protein Folding Problem and Tertiary Structure Prediction, Merz et al., eds., Birkhauser, Boston, pp. 492–495.*
Bork, 2000, Genome Research 10:398–400.*
Skolnick et al., 2000, Trends in Biotech. 18(1):34–39.*
Doerks et al., 1998, Trends in Genetics 14:248–250.*
Smith et al., 1997, nature Biotechnology 15:1222–1223.*
Brenner, 1999, Trends in Genetics 15:132–133.*
Bork et al., 1996, Trends in Genetics 12:425–427.*
Mori et al., "Stimulation of osteoblast proliferation by the cartilage–derived growth promoting factors chondromodulin–I and II", FEBS Letters 406 (1997), pp. 310–314.

* cited by examiner

*Primary Examiner*—Elizabeth Kemmerer
(74) *Attorney, Agent, or Firm*—Kilyk & Bowersox P.L.L.C.

(57) ABSTRACT

A leukocyte activating protein factor or a substance originating therein having an effect of inhibiting bone resorption; and novel medicinal utilization thereof. Use of these novel substances with the bone resorption inhibitory effect makes it possible to provide therapeutic methods efficacious against hypercalcemia, osteoporosis, etc.

20 Claims, 1 Drawing Sheet

SEQUENCE LISTING

```
<160> NUMBER OF SEQ ID NOS: 2

<210> SEQ ID NO 1
<211> LENGTH: 151
<212> TYPE: PRT
<213> ORGANISM: homo sapiens
<220> FEATURE:
<221> NAME/KEY: UNSURE
<222> LOCATION: (58)
<223> OTHER INFORMATION: Xaa=Val or Ile

<400> SEQUENCE: 1

Met Phe Ser Thr Lys Ala Leu Leu Ala Gly Leu Ile Ser Thr
1               5                   10                  15

Ala Leu Ala Gly Pro Trp Ala Asn Ile Cys Ala Gly Lys Ser Ser
                20                  25                  30

Asn Glu Ile Arg Thr Cys Asp Arg His Gly Cys Gly Gln Tyr Ser
                35                  40                  45

Ala Gln Arg Ser Gln Arg Pro His Gln Gly Val Asp Xaa Leu Cys
                50                  55                  60

Ser Ala Gly Ser Thr Val Tyr Ala Pro Phe Thr Gly Met Ile Val
                65                  70                  75

Gly Gln Glu Lys Pro Tyr Gln Asn Lys Asn Ala Ile Asn Asn Gly
                80                  85                  90

Val Arg Ile Ser Gly Arg Gly Phe Cys Val Lys Met Phe Tyr Ile
                95                  100                 105

Lys Pro Ile Lys Tyr Lys Gly Pro Ile Lys Lys Gly Glu Lys Leu
                110                 115                 120

Gly Thr Leu Leu Pro Leu Gln Lys Val Tyr Pro Gly Ile Gln Ser
                125                 130                 135

His Val His Ile Glu Asn Cys Asp Ser Ser Asp Pro Thr Ala Tyr
                140                 145                 150

Leu
151

<210> SEQ ID NO 2
<211> LENGTH: 151
```

-continued

```
<212> TYPE: PRT
<213> ORGANISM: homo sapiens

<400> SEQUENCE: 2

Met Phe Ser Thr Lys Ala Leu Leu Ala Gly Leu Ile Ser Thr
1               5                   10                  15

Ala Leu Ala Gly Pro Trp Ala Asn Ile Cys Ala Gly Lys Ser Ser
                20                  25                  30

Asn Glu Ile Arg Thr Cys Asp Arg His Gly Cys Gly Gln Tyr Ser
                35                  40                  45

Ala Gln Arg Ser Gln Arg Pro His Gln Gly Val Asp Ile Leu Cys
                50                  55                  60

Ser Ala Gly Ser Thr Val Tyr Ala Pro Phe Thr Gly Met Ile Val
                65                  70                  75

Gly Gln Glu Lys Pro Tyr Gln Asn Lys Asn Ala Ile Asn Asn Gly
                80                  85                  90

Val Arg Ile Ser Gly Arg Gly Phe Cys Val Lys Met Phe Tyr Ile
                95                  100                 105

Lys Pro Ile Lys Tyr Lys Gly Pro Ile Lys Lys Gly Glu Lys Leu
                110                 115                 120

Gly Thr Leu Leu Pro Leu Gln Lys Val Tyr Pro Gly Ile Gln Ser
                125                 130                 135

His Val His Ile Glu Asn Cys Asp Ser Ser Asp Pro Thr Ala Tyr
                140                 145                 150

Leu
151
```

BONE RESORPTION INHIBITORS

This application claims the benefit of earlier filed International Application No. PCT/JP99/07152 filed Dec. 20, 1999.

BACKGROUND OF THE INVENTION

1. Field of the Invention

The present invention is concerned to a bone resorption inhibitor consisted of a leukocyte activating protein factor or a substance originating therein. A screening method against therapeutic for hypercalcemia, osteoporosis.

2. Description of the Prior Art

A leukocyte activating protein factor (hereinafter referred to LECT2 [Leukocyte-derived chemotaxinm 2]) has been found as a neutrophil chemotactic factor (Laid-open Patent publication No. Hei8-140683). Gene of human and bovine LECT2s have been cloned and their sequences have also been determined (S. Yamagoe et al., Immunol. Lett. 52, 9–13, 1996 S. Yamagoe et al., Biochem. Biophys. Acta, 1396, 105–113, 1998). mRNA of human LECT2 codes 151 amino acids containing 18 amino acids sequence for its signal peptide. Amino acid sequences of ovine and human LECT2s show the higher homology to min-1 gene product derived from chicken. The min-1 product is contained in promyelocytes in the bone marrow and relates to generating control of oncogne myb, although its biological function has not been determined.

Action of LECT2, which was found as a chemotactic factor, is thought to use for diagnosis, therapy and follow up the diseases such as cancer, because increase of tumoricidal activity and production of interleukins from leukocytes due to activation of neutrophils with LECT2. Now, it is known that LECT2 only acts on neutrophils, action on bone metabolism has not, been reported (Protein, Nucleic Acid and Enzyme-Tanpakushitu-Kakusan-Koso 42, 1086, 1997).

On the other hand, Fujio Suzuki et al. (Y. Hiraki et al., J. biol. Chem. 271, 22657–22662, 1996) isolated Chondromodulin-II, which is approximately 16 kDa protein from chondrocytes of fetal bovine. It is disclosed that Chondromodulin-II shows a promotion for proliferating chondorocytges and its differentiation (Laid open Patent publication No. H5-255398) and that chondromodulin has a promotion for proliferating osteoclast and has an act for activating osteoclast (Laid-open Patent Publication No. H8-27020). Recently, according to study on homology, it was found that Chondromodulin-II is the same as that of LECT2.

Osteoclasts, which are polynuclear large cells, act an adsorpting bone in bone tissues, thereby taking important part in re-modeling bone. Precursor cells will be derived from stem cells, and translocated on bone surface through circulated blood thereby being differentiated to osteoclast. On the other hand, osteoblast are differentiated from pre- cursor cell, which belongs to stroma forming cells such as immature mesenchymal cells, fibroblasts and interstitial cell, and are derived from precursor of different cell line from those of osteoclasts. Bone forms by remodeling according to formation and resorption of bone repeatedly. Organizationally, remodeling of bone is carried out by resorpting, and, then, re-synthesizing bone from osteoblast, under reasonable balance. With aging, the balance change is occurred due to imbalance conditions of the metabolism, the weight of bone is decreased. With the continuation of this condition for long time, bone tissues get weak and cause osteoporosis, destruction of bone or pain in lumbars.

As agents against resorption of bone estrogen, calcitonin, bisphosphate and the like have been used, however side effects are also reported.

Accordingly, highly effective for inhibiting resorption of bone due to osteoclast and highly salty agents have been desired.

SUMMARY OF THE INVENTION

According to hard study, the inventors found the bone resorption inhibitor on osteoclasts, and eminently succeeded the invention.

An object of the present invention is to provide a novel bone resorption inhibitor.

Another object of the present invention is to provide the bone resorption inhibitor containing effective amount of substance derived from LECT2 or LECT2 derived substances.

Further object of the present invention is to provide the bone resorption inhibitor containing LECT2 or LECT2-derived substances involving sequences of amino acid number 1 to 151 or 19 to 151.

Still another object of the present invention is to provide the bone resorption inhibitor containing leukocyte activating protein factor or leukocyte activating protein factor-derived substances.

Still further object of the present invention is to provide screening methods for bone resorption inhibitors derived substances containing leukocyte activating protein factor or leukocyte activating protein factor-derived substances.

Still further object of the present invention is to provide the bone resorption inhibitors showing the inhibitory activity by more than 80% at a concentration of 10 μg/ml in the screening methods pit formation mentioned above for bone resorption inhibitors in the candidate substances.

Still further object of the present invention is also concerned use of leukocyte activating protein factor or leukocyte activating protein factor-derived substances in the production of bone resorption inhibitors.

Still further object of the present invention is also concerned methods for treatment in animals with bone resorption inhibitors derived substances containing leukocyte activating protein factor or leukocyte activating protein factor-derived substances.

A main feature of the present invention is to find that LECT2 or LECT2-derived substances posses bone resorption inhibiting activity.

DESCRIPTION OF THE PREFERRED EMBODIMENT

Figure 1:
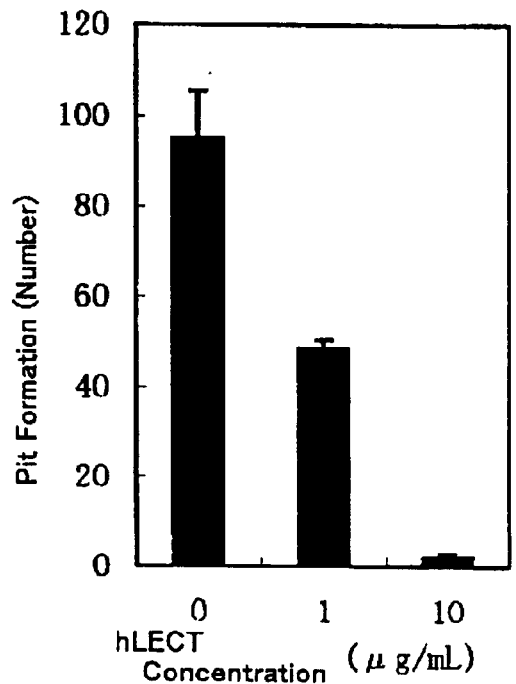
FIG. 1 shows results in the inhibition of bone resorption in unfractionated bone tissue cells with human LECT2 (hereinafter referred to as hLECT2) by the pit formation assay. Horizontal axis shows concentration of hLECT2 and vertical axis shows pit number/ivory slice. hLECT2 showed complete inhibitory activity (100%) at a concentration of 10 μg/ml.

LECT2 in the invention can be purified as follows.
Purification of LECT2.

LECT2 in culture fluid of cells such as leukemic cells was concentrated with CM-Sepharose CL-6B (Pharmacia Biotech, Uppsala, Sweden) and DEAE-Sepharose (Pharmacia Biotech), CM-Sepharose CL-6B, hydroxylapatite and a reverse-phase column (Vydac C4 column 304-2151, 6××250 mm) on HPLC. For example, leukocyte activating protein factor can also be purified from the culture fluid of SKW-3 leukemic cells stimulated with PHA for release of leukocyte activating protein factor into the fluid.

LECT2 or LECT2-derived substances can also be purified by a gene technology (Laid-open Patent publication No. Hei 8-140683, Hei 10-146189). For example, transformant cells may be produced with pMAL-TM-C or pGEX-3X as a vector. As host cells bacteria such as *E. coli*, yeast and animal cells may be used. The animal cells, such as Chinese hamster CHO cells, monkey CVI cells, monkey CVI/293 cells, monkey COS cells, mouse fibroblast cells, mouse C127 cells, mouse 3T3 cells, mouse L-929 cells, human ReLa cells and human SKW-3 cells, which can express the recombinant plasmid encoding human LECT2, may be exemplified.

As regarding yeast, those established in a commercial production process, such as bread yeast, are convenient. In view of the industrial process, yeast-secreting line may be the most beneficially used.

Culture of these cells, purification of the protein in the invention from culture fluid, preparation of recombinant plasmid, and transformant cells, and usual purification of the protein from the transformant cells, can be used in a well-known manner.

LECT2-derived substances have inhibitory activity showing bone resorption, indicating the substance, is not specifically limited. The substances showing inhibitory activity of bone resorption are also involved in mutations such as deletion, replace, addition, and/or insertion on one or several sites in the amino acid (Ulmer, K. M., Science, 219, 666, 1983) of LECT2. Further, LECT2-derived substances are also involved in chimera protein, fusion protein, partial deletion protein, partial modified and chemically modified protein. Further, peptide or low molecular weight molecules preferred according to the primary-, secondary-, tertiary- and 3D-structures of LECT2 or LECT2-derived substances is also involved in the substances (Laid-open Patent Publication Nos. H5-255398 and H8-140683, WO/16177) (Li et al., Bioorganic & Medical Chemistry, 4, 1421–1427, 1996) (S. Yamagoeet al. B.B.R.C. 237, 116–120, 1997: Monoclonal antibody to a recombinant LECT2). Source of LECT2 or LECT2-derived substances is not restricted in species of animal if they have bone resorption inhibitory activity, but human is preferred for the antigenecity.

In the present invention, the bone resorption inhibitory activity of LECT2 or LECT2-derived substances can be assayed for example as follows. Bone resorption inhibitory activity of LECT2 or LECT2-derived substances is assayed by the inhibition of pit formation during incubation overnight by osteoclast cells isolated from rabbit are placed on ivory slice (Takeda et al. Bone and Minearl 17, 347–359, 1992) (Kameda, et al, Nihon Ykuri Zasshi 109, 74–84, 1997). Substances showing bone resorption inhibitory activity can be selected by the screening using percent inhibition of pit formation. For example, the substance showing 80% of present inhibition under concentration of 10 g/ml may be selected.

As bone diseases osteoporosis for use of substances having bone resorption inhibitory activity mentioned in the invention, hypercalcemia, hyperparathyroid and Bechet are listed.

When use of substances having bone resorption inhibitory activity mentioned in the present invention, 0.005–10 mg/kg or 0.01–3 mg/kg in preferentially with separation into 3 times in the dosage may be made, and the dosage can be increased or decreased from the recommendation according to chemical character, disease state and age and etc.

Constituents of pharmaceutical compositions, in addition to the active agents described herein, include those generally known in the art for the various administration methods used. For example, oral forms generally include powders, tablets, pills, capsules, lozenges and liquids. Similarly, intravenous, intraperitoneal or intramuscular formulations will generally be dissolved or suspended in a pharmaceutically acceptable carrier, e.g., water, buffered water, saline and the like. Additionally, these compositions may include additional constituents which may be required to approximate physiological conditions, such as pH adjusting and buffering agents, tonicity adjusting agents, wetting agents and the like. For solid compositions, conventional nontoxic solid carriers may be used which include, e.g., pharmaceutical grades of mannitol, lactose, starch, magnesium stearate, sodium saccharin, talcum, cellulose, glucose, sucrose, magnesium carbonate and the like.

According to the present invention, it was found that LEC2 contained the inhibitory activity against bone resorption, and therapeutic treatment for hypercalcemia and osteoporosis etc. could be presented. Further, the screening method to get bone resorption substance could be also presented.

EXAMPLES

The present invention is further explained by way of example as follows.

This is an example for practical use; the invention is not restricted by this example.

Example 1

(1) Unfractionated Cells

Infant rabbit about 110 g 10 day-old was sacrificed under diethyl ether as anesthetics. After removal of soft tissues, bone from 4 legs was isolated. And then the bone was minced in a α-minimal essential medium (α-MEM) containing 5% fetal bovine serum (FBS). The sufficiently minced bone and the medium was mixed with Vortex mixer to remove cells stacked on the bone. After 2 minutes, the unfractionated cells in the supernatant were collected.

(2) Pit Assay

Ivory slice was prepared by cutting ivory into the disk-form piece (6 mm in diameter) with 20–40 μm in depth, and then sterilized with ultrasonic treatment of 70% ethanol. After each ivory slice was washed with phosphate buffered saline (PBS) and alpha-MEM medium, it was transferred to 96-well plate with 200 μl of culture medium containing α-MEM and 5% FBS. After incubation of the plate in a $CO_2$ incubator (5%$CO_2$ and 96% air) for 2 hrs at 37° C., the culture medium was removed from the well completely, culture medium containing hLECT2 at a several concentrations and $5 \times 10^5$ cells of unfractionated bone cells were added to the well. After incubation again under the same conditions for 18 hours, cells attached on the ivory slice were completely removed with rubber polisher. Then, the slice was stained with acidic hematoxyline solution for few minutes at room temperature. Bone resorption activity in the slice was measured by number of pit with a microscopic observation.

FIG. 1 shows results in inhibition of bone resorption in unfractionated bone tissue cells with human LECT2

(hLECT2) by the pit formation assay. Horizontal axis shows concentration of hLECT2 and vertical axis shows pit number/ivory slice. hLECT2 showed complete inhibitory activity at a concentration of 10 Ig/ml.

Example 2

(1) Purification of Osteoclast Cells

The unfractionated cells obtained in the Example 1 were plated into a plastic dish, which were coated with collagen gel (Nitta Zeratinin Cell Matrix Type I, Co., Tokyo, Japan) the supernatant were collected. After incubation of the plate in a $CO_2$ incubator (5%$CO_2$ and 95% air) for 2 hrs at 37° C., the culture medium was removed from the well completely, the dish was washed with PBS three times to remove the cells on the gel. Then, the dish was washed with PBS containing 0.01% pronase E and 0.02% EDTA solution three times again. Cells without osteoclast were completely removed with the incubation for 5 minutes at room temperature in PBS containing collagenase. The remained cells containing attached molecules on the gel in the dish were collected after adding PBS containing 0.1% collagenase and standing for 10 minutes at room temperature to obtain cell suspending solution in which osteoclast was exclusively contained.

(2) Pit Assay

Figure 2:
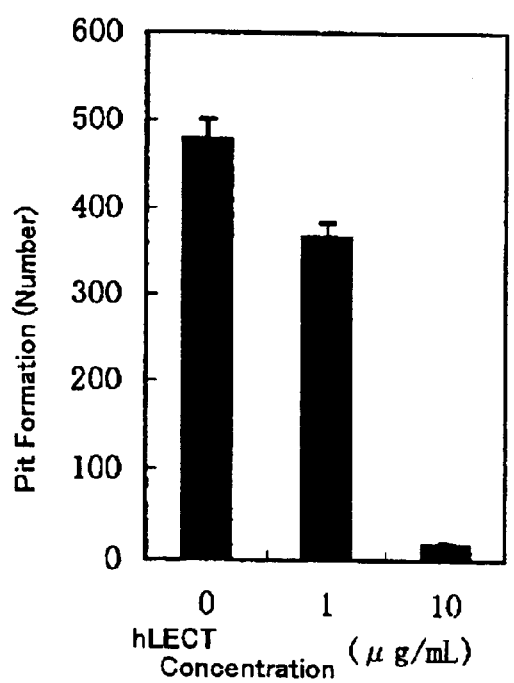
FIG. 2 shows results in the inhibition of bone resorption in purified osteoclast cells with hLECT2 by the pit formation assay. As well as results in the assay using unfractionated bone tissuecells; hLECT2 showed completely inhibitory activity (100%) at a concentration of 10 μg/ml using purified osteoclast cells.

Pit assay was preformed using the ivory slice and the culture medium by the same procedures as that described in the Example 1 with exception for use of 3000 purified osteoclast cells in a well, instead of the unfractionated bone cells. FIG. 2 shows results in inhibition of bone resorption in purified osteoclast cells with human LECT2 (hLECT2) by the pit formation assay. As well as results in the assay using unfractionated bone tissue cells; hLECT2 showed completely inhibitory activity at a concentration of 10 µg/ml using purified osteoclast cells.

Example 3

(Acute Toxicity)

Substances having sequences of amino acid number 19 to 151 of the leukocyte activating protein factor prepared by the well-known procedures were injected into venous of 5 ddY mice (body weight 20±1 g) at dosage 0.1 mg/g.

What is claimed is:

1. A bone resorption inhibitor composition comprising leukocyte activating protein factor or leukocyte activating protein factor-derived substances having an amino acid sequence of SEQ ID NO. 2, that is produced utilizing gene technology in an amount effective for bone resorption inhibitory activity.

2. A bone resorption inhibitor composition comprising leukocyte activating protein factor or leukocyte activating protein factor-derived substances, wherein the leukocyte activating protein factor has sequences of amino acid number 19 to 151 of SEQ ID NO. 2.

3. The bone resorption inhibitor composition according to claim 1, wherein the leukocyte activating protein factor or leukocyte activating protein factor-derived substances inhibits against osteoclast cell activity.

4. The bone resorption inhibitor composition according to claim 1, wherein said substances have an inhibitory activity of more than 80% at a concentration of 10 µg/ml using percent inhibition of pit formation.

5. A screening method for bone resorption inhibitor derived substances containing leukocyte activating protein factor or leukocyte activating protein factor-derived substances having an amino acid sequence of SEQ ID NO. 1, which are purified from the source of these substances, or which are prepared by or synthesized based on the information of these substances, comprising providing said derived substances and deterring bone resorption inhibitory activity of the derived substances using percent inhibition of pit formation.

6. A method of producing bone resorption inhibitor comprising using leukocyte activating protein factor or leukocyte activating protein factor-derived substances having an amino acid sequence of SEQ ID NO. 1 in the production of bone resorption inhibitors.

7. A method for bone resorption inhibiting in an animal comprising administering to said animal an effective amount of bone resorption inhibitor derived substances containing leukocyte activating protein factor or leukocyte activating protein factor-derived substances having an amino acid sequence of SEQ ID NO. 1.

8. The bone resorption inhibitor composition according to claim 2, wherein the leukocyte activating protein factor or leukocyte activating protein factor-derived substances inhibits against osteoclast cell activity.

9. The bone resorption inhibitor composition according to claim 2, wherein said substances have an inhibitory activity of more than 80% at a concentration of 10 µg/ml using percent inhibition of pit formation.

10. The bone resorption inhibitor composition according to claim 3, wherein said substances have an inhibitory activity of more than 80% at a concentration of 10 µg/ml using percent inhibition of pit formation.

11. The method of claim 5, wherein the sample is obtain from an animal.

12. The method of claim 11, wherein the animal is a human.

13. The method of claim 7, wherein the animal is a human.

14. A method of producing bone resorption inhibitor comprising:
    providing leukocyte activating protein factor or leukocyte activating protein factor-derived substances; and
    using the leukocyte activating protein factor or the leukocyte activating protein factor-derived substances in the production of bone resorption inhibitors, wherein the leukocyte activating protein factor or leukocyte activating protein factor-derived substance has an amino acid sequence of SEQ ID NO. 1.

15. A method for bone resorption inhibiting in an animal comprising:

providing a bone resorption inhibitor derived substance containing at least one leukocyte activating protein factor or leukocyte activating protein factor-derived substance; and administering to said animal an effective amount of a bone resorption inhibitor derived substance containing leukocyte activating protein factor or leukocyte activating protein factor-derived substances, wherein the bone resorption inhibitor derived substances containing leukocyte activating protein factor or leukocyte activating protein factor-derived substances has an amino acid sequence of SEQ ID NO. 1.

16. The bone resorption inhibitor composition according to claim 1, wherein the composition is produced utilizing pMAL-TM-C or pGEX-3X, or both, as a vector.

17. The bone resorption inhibitor composition according to claim 1, wherein the composition is produced utilizing *E. coli* or yeast cells, or both, as host cells.

18. The bone resorption inhibitor composition according to claim 1, wherein the composition is present in an aqueous solution.

19. The bone resorption inhibitor composition according to claim 1, wherein said bone resorption inhibitor composition further comprises a carrier.

20. The bone resorption inhibitor composition according to claim 1, wherein the composition is in contact with unfractionated bone tissue cells.

* * * * *

UNITED STATES PATENT AND TRADEMARK OFFICE
CERTIFICATE OF CORRECTION

PATENT NO. : 6,723,696 B1
DATED : April 20, 2004
INVENTOR(S) : Suzuki et al.

It is certified that error appears in the above-identified patent and that said Letters Patent is hereby corrected as shown below:

Column 7,
Line 62, "deterring" should read -- determining --.

Signed and Sealed this

Twenty-third Day of November, 2004

JON W. DUDAS
*Director of the United States Patent and Trademark Office*